US006987182B2

(12) United States Patent
Resch et al.

(10) Patent No.: US 6,987,182 B2
(45) Date of Patent: Jan. 17, 2006

(54) PROCESS FOR PRODUCING COLD-GELLING HYDROCOLLOIDS

(75) Inventors: Jeffrey J. Resch, Raleigh, NC (US); Christopher R. Daubert, Apex, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 10/397,653

(22) Filed: Mar. 26, 2003

(65) Prior Publication Data

US 2004/0192907 A1    Sep. 30, 2004

(51) Int. Cl.
*C07H 5/04* (2006.01)

(52) U.S. Cl. .................... 536/123; 536/123.1; 536/4.1; 536/18.2; 536/18.6; 536/63; 536/103; 536/112; 426/573; 426/92; 426/93; 604/368; 514/54; 424/445

(58) Field of Classification Search ............... 536/123, 536/123.1, 4.1, 18.2, 18.6, 63, 103, 112; 426/573, 92, 93; 604/368; 514/54; 424/445
See application file for complete search history.

(56) References Cited

U.S. PATENT DOCUMENTS 6,455,512 B1 * 9/2002 Ward ........................... 514/59

FOREIGN PATENT DOCUMENTS

JP          57028102       * 2/1982

* cited by examiner

Primary Examiner—James O. Wilson
Assistant Examiner—Devesh Khare
(74) Attorney, Agent, or Firm—Myers Bigel Sibley & Sajovec

(57) ABSTRACT

A dry hydrocolloid powder with cold-gel capabilities is produced by: dissolving a hydrocolloid comprising polysaccharide chains in an aqueous solution; heating the dissolved hydrocolloid solution to a temperature and for a time sufficient to induce a substantial alteration in the tertiary structure of the polysaccharide chains of the hydrocolloid; cooling the dissolved hydrocolloid solution to a temperature and for a time sufficient to substantially return the polysaccharide chains of the hydrocolloid to their original tertiary structure, wherein the polysaccharide chains form a gelling network; and drying the cooled hydrocolloid solution to form a dry powder. In some embodiments, the dry powder has a viscosity of between about 10 and 40 mPa-s when reconstituted in a 2% weight/weight solution at 25 degrees C. In other embodiments, the dry powder has a water absorption of greater than 20 g $H_2O$/g powder.

21 Claims, 2 Drawing Sheets

PROCESS FOR PRODUCING COLD-GELLING HYDROCOLLOIDS

FIELD OF THE INVENTION

The present invention is directed generally to food additives, and more particularly to food additives that thicken, suspend or gel foods.

BACKGROUND OF THE INVENTION

Hydrocolloids are substances often used in the stabilizing, thickening and gelling in food and other products. Hydrocolloids are large molecular weight polysaccharides that can gel through interlinking of their polymer chains. In gelation, water is trapped within an intertwined network of polymer chains. Hydrocolloids can gel in a variety of ways, including heat-cool cycling and the addition of chemical agents.

One such hydrocolloid, carrageenan, is a family of linear sulfated food grade polysaccharides typically obtained from red seaweed. Carrageenans are present in the seaweed as gels under natural environmental conditions and have the unique ability to form an almost infinite variety of gels at room temperature, rigid or compliant, tough or tender with high or low melting point. Carrageenan solutions can thicken, suspend and stabilize particulates as well as colloidal dispersions and water/oil emulsions. The solutions are pseudoplastic, but quickly rebuild viscosity and suspending power upon standing. Carrageenan can be used in a wide variety of foods, including sauces and gravies, processed meats and cheeses, chocolate milk, dressings, desserts, and the like.

The carrageenan family has three main types (known as kappa, iota and lambda), which are well differentiated in terms of their gelling properties and protein reactivity. Kappa carrageenans typically produce strong rigid gels, while those made with iota products are flaccid and compliant. Although lambda carrageenans do not gel in water, they can interact strongly with proteins to stabilize a wide range of dairy products. Exemplary chemical structures for kappa, iota, and lambda carrageenan are disclosed in A. Imeson, *Thickening and Gelling Agents for Food*, (Blackie Academic & Professional 1992), which is hereby expressly incorporated by reference as though set forth in full herein. Kappa and iota carrageenans form helical tertiary structures, which tend to destabilize in the presence of sulfate substituents (it is the higher percentage of sulfate groups in lambda carrageenan that is believed to prevent it from gelling).

Production of carrageenan typically begins with the extraction of the material from the seaweed with alkaline aqueous solutions at elevated (i.e. about 50° C.) temperature. After extraction, the carrageenan is clarified to remove cellulose, (typically by filtration), concentrated, and recovered (often through an alcohol precipitation on freeze-thawing technique). The carrageenan is then typically ground to a powder for use. Exemplary procedures are described in U.S. Pat. No. 6,063,915, the disclosure of which is hereby incorporated herein in its entirety. In many instances, different carrageenans are blended in known percentages (e.g., 45 percent kappa, 45 percent iota and 10 percent lambda) prior to use in food.

Preparation of a carrageenan gel has typically commenced with the dispersion of the carrageenan powder in cold water, which is then heated to a temperature above 75° C. to dissolve. The dissolution disentangles the polymer chains and uncoils the helices thereof. The solution is then cooled to form a gel, during which time the helices recoil, thereby causing the carrageenan molecules to entangle and cross-link (electrostatic bonding between the sulfate groups and ions in the solution can also occur). This cross-linking increases the ability of the carrageenan to gel.

In some instances, the gelation of the carrageenan solution (and, in turn, the thickening or other alteration of the foodstuff to which it is added) is carried out during the preparation of the food itself (for example, if carrageenan is used to thicken a pudding, the pudding and carrageenan are heated, then cooled, at which point the pudding gels). However, in some instances, it would be convenient if carrageenan would gel and thicken without undergoing heating. This behavior would also be desirable for ready-to-eat chilled foods. It would also be convenient if other hydrocolloids could be similarly prepared.

SUMMARY OF THE INVENTION

The present invention can provide a cold-gelling hydrocolloid product that may be used advantageously to thicken foods such as puddings, ice cream, milk shakes, custards, gels and the like. As a first aspect, the present invention is directed to a dry hydrocolloid powder with cold-gel capabilities. The powder is produced by: dissolving a hydrocolloid comprising polysaccharide chains in an aqueous solution, the polysaccharide chains having an original tertiary structure; gelling the dissolved hydrocolloid solution under conditions sufficient to form a gelling network; and drying the hydrocolloid gel network to form a dry powder. In some embodiments, the dry powder has a solution viscosity of between about 10 and 40 mPa-s when reconstituted in a 2% weight/weight solution at 25° C.

As a second aspect, the present invention is directed to a dry hydrocolloid powder with cold-gel capabilities. The powder is produced by: dissolving a hydrocolloid comprising polysaccharide chains in an aqueous solution; heating the dissolved hydrocolloid solution to a temperature and for a time sufficient to induce a substantial alteration in the tertiary structure of the polysaccharide chains of the hydrocolloid; cooling the dissolved hydrocolloid solution to a temperature and for a time sufficient to substantially return the polysaccharide chains of the hydrocolloid to their original tertiary structure, wherein the polysaccharide chains form a gelling network; and drying the cooled hydrocolloid solution to form a dry powder. In some embodiments, the dry powder has a viscosity of between about 10 and 40 mPa-s when reconstituted in a 2% weight/weight solution. In other embodiments, the dry powder has a water absorption value of greater than 20.0 g $H_2O$/g powder when reconstituted in an excess of distilled water. Carrageenan is a particularly suitable hydrocolloid. These powders can be added to ingredients of edible food products to increase the viscosity thereof.

As a third aspect, the invention is directed to a process for producing a dry powder. The process comprises: heating a dissolved hydrocolloid solution to a temperature and for a time sufficient to induce a substantial alteration in the tertiary structure of the polysaccharide chains of the hydrocolloid; cooling the dissolved hydrocolloid solution to a temperature and for a time sufficient to substantially return the polysaccharide chains of the hydrocolloid to their original tertiary structure, wherein the polysaccharide chains form a gelling network; and powdering the cooled hydrocolloid network to form a dry powder.

As a fourth aspect, the invention is directed to a process for thickening an edible food product, comprising: heating an aqueous hydrocolloid solution to a temperature and for a time sufficient to induce a substantial alteration in the tertiary structure of the polysaccharide chains of the hydrocolloid; cooling the dissolved hydrocolloid solution to a temperature and for a time sufficient to substantially return the polysaccharide chains of the hydrocolloid to their original tertiary structure, wherein the polysaccharide chains form a gelling network; and mixing the aqueous hydrocolloid network with the remaining ingredients of the edible food product, the aqueous hydrocolloid solution being included in an amount sufficient to increase the viscosity of the edible food product. This technique avoids the steps of powdering and reconstituting the gelled, cooled hydrocolloid.

DETAILED DESCRIPTION OF THE INVENTION

Figure 1:
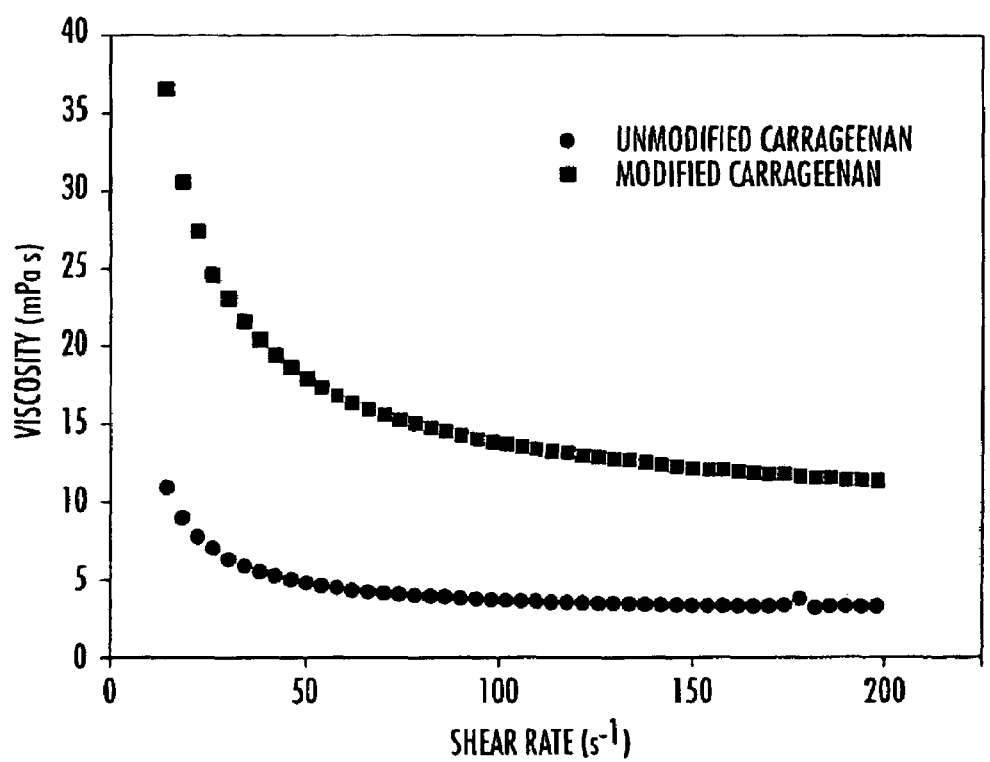
FIG. 1 is a graph plotting viscosity as a function of shear rate at 25° C. for 2 percent w/w carrageenan gels for control hydrocolloid and hydrocolloid modified according to embodiments of the present invention.

The present invention will be described more particularly hereinafter. The invention is not intended to be limited to the illustrated embodiments; rather, these embodiments are intended to fully and completely disclose the invention to those skilled in this art. Like numbers refer to like components throughout, and certain dimensions and thicknesses may be exaggerated for clarity.

As described above, the present invention is directed to the use of a hydrocolloid-based thickening agent. As used herein, a "hydrocolloid" is intended to include any large molecular weight polysaccharide known to form a gel in water. Exemplary hydrocolloids include xanthan gum, guar gum, locus bean gum, tara gum, agar, furceltaran, sodium alginate, pectin, gum arabic, and carrageenan. Other hydrocolloids include carboxy-methylcellulose, methylcellulose, and hydroxypropylmethylcellulose, As used herein, "carrageenan" is intended to include any of the family of linear sulfated food grade polysaccharides typically obtained from red seaweed. It is preferred that the carrageenan be provided in an extracted form. The carrageenan can be kappa, iota or lambda carrageenan, or a blend of two or three of these forms. Particularly suitable is a blend comprising kappa carrageenan and at least one of iota and lambda carrageenan. An exemplary carrageenan blend suitable for use with the present invention is SeaGel DP 437, a commercial blend available from FMC Corporation (Philadelphia, Pa.).

The hydrocolloids employed in embodiments of the present invention can be provided in solid form (such as a powder, cake, particle, or the like) or in solution (for example, as an aqueous solution), and can be produced in any production manner known to those skilled in this art. A suitable production technique for carrageenan is described generally in U.S. Pat. No. 6,063,915 to Hansen et al., supra.

According to embodiments of the present invention, the hydrocolloid is dissolved in an aqueous solution. As used herein, an "aqueous solution" is intended to mean solutions that include water as the predominant solvent. Also, the aqueous solutions may comprise distilled or deionized water, or alternatively may include ionic components (such as salts like sodium chloride or potassium chloride, preferably in a concentration of between about 0.1 and 2 percent) that may impact gelation. The aqueous solutions may be of a neutral, acidic or basic pH, with solutions having a pH of between about 6.0 and 8.0 being preferred.

The hydrocolloid is typically dissolved in the aqueous solution in a concentration of between about 0.01 and 10 percent by weight, and preferably in a concentration of between about 0.1 and 5 percent by weight, although other concentrations of hydrocolloid may also be suitable for use with the present invention. It may be desirable to enhance or expedite dissolution of the hydrocolloid through agitation or stirring of the solution.

The dissolved hydrocolloid solution is gelled. For some hydrocolloids, such as carrageenan, agar, furceltaran, pectin, gum arabic, xanthan gum, and locust bean gum, gelling follows a thermal mechanism, and is carried out by heating followed by cooling. For other hydrocolloids, such as sodium alginate and low methoxyl pectin, gelling is carried out by a chemical mechanism, so the addition of a chemical reagent (for example, calcium) causes gelation.

For thermally gelled hydrocolloids, the dissolved hydrocolloid solution is heated, typically to a temperature of between about 50 and 95 degrees C. (a temperature for carrageenan of between about 70 and 90 degrees C. is preferred). While not wishing to be bound by any theory of operation of the invention, the inventors believe that this heating causes the polysaccharide chains of the hydrocolloid, and in particular carrageenan, to disentangle from one another and substantially alter or denature their tertiary structure (for example, in the case of carrageenan, the helices of the carrageenan tend to at least partially uncoil). As used herein, "substantially alter" or "denature" means to sufficiently change the hydrocolloid solution so that a gelling network is formed in this or a subsequent step (such as cooling). Heating can be achieved through techniques known to those skilled in this art. This heating should be carried out for a duration sufficient to disentangle the polysaccharide chains, which is typically between about 1 and 120 minutes (depending on the size of the batch of solution), and may include stirring or other agitation, which can promote disentanglement.

After heating, a thermally gelled hydrocolloid solution is cooled, typically to or below its gelation temperature (in many cases, the hydrocolloid gelation temperature will be between about 0 and 60 degrees C., and for carrageenan the gelation temperature is typically between about 30 and 50 degrees C.). Cooling can be active (i.e., with chilling or refrigeration) or passive (i.e., the heated solution can be allowed to stand until it reaches the desired temperature). While not wishing to be bound by any theory of operation, the inventors theorize that cooling causes the polysaccharide chains of the hydrocolloid to substantially regain or return to their original tertiary structure, and the re-entanglement of the chains causes them to form a gelling network that is able to trap water. In the instance of carrageenan, the polysaccharide chains recoil into helices. The cooled hydrocolloid solution is typically maintained at temperature until subsequent processing (either powdering or addition into a recipe) occurs.

After cooling, in some embodiments of the invention, the hydrocolloid network is dried to form a dry powder. Drying can be carried out by any technique known to those skilled in this art to be suitable for producing a dry powder from a solution. Exemplary techniques include spray drying, freeze drying, grinding and crumbling. The dry powder may have virtually any particle size, although a particle size between about 1 and 10 µm is preferred.

The dry powder described above can be combined with other ingredients, such as emulsifying agents, stabilizing agents, anti-caking, anti-sticking agents and the like. Representative stabilizing agents are gums, certain proteins such as gelatins, and certain chemical derivatives of cellulose, and emulsifiers like lecithin.

The dry powder can be combined with a cold water-soluble protein to provide a thickening agent or fat substitute with both protein and carbohydrate components, depending upon particular dietary and cost considerations. See, e.g., U.S. Pat. No. 6,261,624 to Hudson et al., the disclosure of which is hereby incorporated herein by reference in its entirety. A cold water-soluble protein may be included in the dry powder in any suitable amount such as from 1 or 2 percent to 80 or 90 percent by weight to provide a combination protein and carbohydrate-based thickening agent or fat substitute.

The dry powder produced by the inventive process can have very desirable properties as a thickening agent. For example, when reconstituted in a 2 percent weight/weight solution in deionized water, a dry carrageenan powder can have a viscosity of between about 10 and 40 mPa-s at 25 degrees C. This viscosity can be raised with the addition of between about 0.1 and 2.0 percent of ionic components such as KCl. Also, the dry powder may have a water absorption value (as determined by the water absorption procedure described below) of greater than 20.0 g $H_2O$/g powder when reconstituted under those conditions. Once in powdered form, the carrageenan or other hydrocolloid powder can be easily stored for long periods in conventional sealed (i.e., airtight) containers.

The properties set forth above can enable the dry powder to be used as a thickening agent, even under cold-setting conditions. When used as a thickening agent, the powder is combined with the other ingredients of the food product in an amount sufficient to thicken or increase the viscosity of the food product (typically 1 or 2 percent to 50 or 60 percent by weight of the total weight of the product). The powder of the invention may of course serve multiple functions in a single food, as a binder, and/or thickening agent, to facilitate foaming, etc., and identification of one function herein is not intended to exclude that the ingredient is performing other functions.

The typical solid food product will constitute from 1 or 2 percent to 50, 60, or 70 percent by weight water (from all sources), or more. The typical liquid (including thickened liquid) food product will typically constitute 40 or 50 percent to 90, 95 or even 99 percent by weight water (from all sources). Other ingredients of a solid food product will typically constitute from 10 or 20 percent to 50, 60 or 70 percent by weight. Other ingredients of a liquid (including thickened liquid) food product will typically constitute from 1 or 2 percent up to 40 or 50 percent by weight, and occasionally more. These percentages are provided as general guidelines only; sometimes water is included in the weight of "dry" ingredients which are not fully dehydrated, and of course in no case do the total amounts of all ingredients exceed 100 percent, thus, it is preferred to define food products of the invention simply by reference to the amount by weight of the dry powder protein preparation added thereto.

The dry powder may be included in the preparation of cold-served foods, like chilled dairy products (such as ice cream, shakes, puddings, and custards), gelatins, salad dressings, processed meat and cheese products, jellies and jams, chocolate milk, syrups, pie fillings, dips, spreads, icings, and condiments. Alternatively, the dry powder can be used as a thickening agent for dysphagia patients to assist with swallowing.

In some embodiments, after cooling of the hydrocolloid solution, it may be added directly into foods during their preparation. This process can shorten the production cycle of such foods by eliminating the powdering process; however, the cooled solution may have a much shorter shelf life than the aforementioned dry powder.

The invention will now be described in greater detail in the following non-limiting examples.

EXAMPLE 1

Sample Preparation

Test samples were prepared by heating a one liter aqueous solution while stirring in measured amounts of kappa carrageenan (2 percent (w/w)) and KCl (0.5 percent (w/w)). The test sample was cooled to 65° C. and maintained. A spray dryer (Anhydro, Attleboro Falls, Mass.) was purged and equilibrated by pumping a small amount of water at 3 L/hr. The spray dryer operated at 15 psi with an interior temperature of 88° C. and an outlet temperature of 32° C. After purging, the spray dryer was used to pump a 1000 g dispersion of each sample, and the sample was collected and weighed.

EXAMPLE 2

Viscosity Testing on Spray-Dried Carrageenan

A. Materials and Methods

Samples from each spray-dryer run described above in Example 1 were rehydrated as 2% (w/w) dispersions. A 2% (w/w) dispersion was also generated with unmodified carrageenan with a KCl concentration of 0.5% (w/w). The samples were allowed to sit for 24 hours. The viscosity of the samples at 25° C. was then measured using a StressTech Controlled Stress Rheometer (Lund, Sweden).

B. Results

Figure 2:
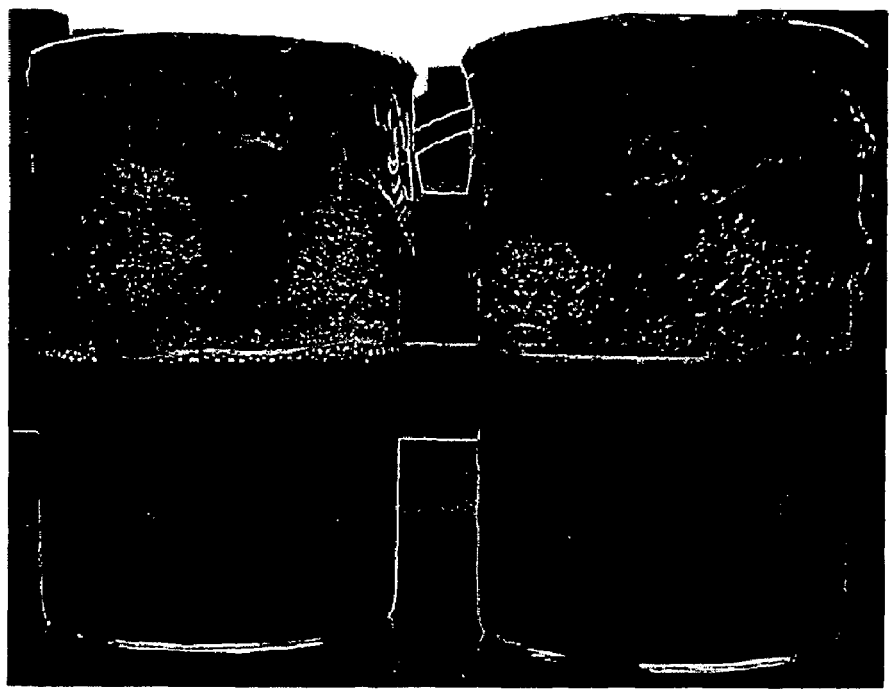
FIG. 2 is a photograph showing 2 percent w/w gels of unmodified carrageenan powder and carrageenan powder according to embodiments of the present invention, wherein it can be seen that the modified carrageenan gel showed no appreciable phase separation.

The results of the viscosity testing are displayed in FIG. 1. The modified dispersions (i.e., those produced by the spray dryer) showed viscosity levels that are at least two times higher than that of the control dispersion. It was also noted that the samples were dispersed much easier than the control dispersion, and that phase separation was not observed with the modified carrageenans (FIG. 2). The mechanism for the improved gelation and dispersability is hypothesized to be that the matrix structure formed before the drying of the gel is somewhat maintained in the powder and rehydrated with the introduction of water to the product.

EXAMPLE 3

Water Absorption Testing

Samples of unmodified carrageenan powder and carrageenan powder prepared as described in Example 1 above were weighed, then placed in separate beakers; the sample amount was slightly less than 1 g. An excess amount of distilled water (about 40–50 mL) was added to each beaker to hydrate the samples. After 24 hours, the excess water was decanted from the beakers. The gelled solutions were then weighed.

A "water absorption value" was then calculated for each sample using the following formula:

$$WA = [W_{(H2O+powder)} - W_{(powder)}] / W_{(powder)}$$

wherein WA is the water absorption value, $W_{(H2O+powder)}$ is the weight of the gelled solution, and $W_{(powder)}$ is the weight of the sample prior to gelling.

The results of the testing are displayed in Table 1.

TABLE 1

|  | Sample # | Water Absorption (g H2O/g powder) |
|---|---|---|
| Modified Carrageenan | 1 | 29.08 |
|  | 2 | 30.35 |
|  | 3 | 24.05 |
|  | 4 | 24.15 |
| Unmodified Carrageenan | 1 | 15.39 |
|  | 2 | 15.17 |

These results indicate that the water absorption of the modified carrageenan was greater than 20 g H2O/g powder, and was as much as twice the magnitude of the water absorption of the unmodified carrageenan.

The foregoing embodiments are illustrative of the present invention, and are not to be construed as limiting thereof. Although exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

What is claimed is:

1. A dry hydrocolloid product useful as a thickening agent, the product comprising a dry powder produced with a viscosity of between 10 and 40 mPa-s when reconstituted in a 2% weight/weight solution at 25 degrees C. produced by the process of:
   dissolving a hydrocolloid comprising polysaccharide chains in an aqueous solution, the polysaccharide chains having an original tertiary structure;
   gelling the dissolved hydrocolloid solution under conditions sufficient to form a gelling network; and
   drying the hydrocolloid network to form a dry powder.

2. The dry hydrocolloid product defined in claim 1, wherein the aqueous solution includes ionic components in a weight/weight concentration of between about 0.1 and 2 percent.

3. The dry hydrocolloid product defined in claim 1, wherein the dry powder has a particle size of between about 1 $\mu$m and 10 $\mu$m.

4. The dry hydrocolloid product defined in claim 1, wherein the dry powder has a water absorption of greater than 20 g H$_2$O/g powder.

5. The dry hydrocolloid product defined in claim 1, wherein the drying comprising spray drying.

6. The dry hydrocolloid product defined in claim 1, wherein the drying comprising freeze drying.

7. The dry hydrocolloid product defined in claim 1, wherein the hydrocolloid comprises carrageenan.

8. The dry hydrocolloid product defined in claim 7, wherein the carrageenan comprises kappa-carrageenan.

9. The dry hydrocolloid product defined in claim 8, wherein the carrageenan further comprises at least one of lambda-carrageenan and iota-carrageenan.

10. The dry hydrocolloid product defined in claim 7, wherein the aqueous solution includes ionic components in a weight/weight concentration of between about 0.1 and 2 percent.

11. The dry hydrocolloid product defined in claim 7, wherein the dry powder has a particle size of between about 1 $\mu$m and 10 $\mu$m.

12. The dry hydrocolloid product defined in claim 7, wherein the drying comprising spray drying.

13. The dry hydrocolloid product defined in claim 7, wherein the drying comprising freeze drying.

14. A dry hydrocolloid product useful as a thickening agent, the product comprising a dry powder produced by;
   dissolving a hydrocolloid comprising polysaccharide chains in an aqueous solution, the polysaccharide chains having an original tertiary structure;
   heating the dissolved hydrocolloid solution to a temperature and for a time sufficient to substantially alter the tertiary structure of the polysaccharide chains of the hydrocolloid;
   cooling the dissolved hydrocolloid solution to a temperature and for a time sufficient to substantially return the polysaccharide chains of the hydrocolloid to the original tertiary structure so that the polysaccharide chains form a gelling network; and
   drying the cooled hydrocolloid solution to form a dry powder;
   wherein the dry powder has a water absorption of greater than 20 g H$_2$O/g powder.

15. The dry hydrocolloid product defined in claim 14, wherein the hydrocolloid comprises carrageenan.

16. The dry hydrocolloid product defined in claim 15, wherein the carrageenan comprises kappa-carrageenan.

17. The dry hydrocolloid product defined in claim 16, wherein the carrageenan further comprises at least one of lambda-carrageenan and iota-carrageenan.

18. The dry hydrocolloid product defined in claim 14, wherein the aqueous solution includes ionic components in a weight/weight concentration of between about 0.1 and 2 percent.

19. The dry hydrocolloid product defined in claim 14, wherein the dry powder has a particle size of between about 1 $\mu$m and 10 $\mu$m.

20. The dry hydrocolloid product defined in claim 14, wherein the drying comprising spray drying.

21. The dry hydrocolloid product defined in claim 14, wherein the drying comprising freeze drying.

* * * * *